United States Patent [19]

Frech et al.

[11] 4,283,373

[45] Aug. 11, 1981

[54] METHOD FOR REMOVAL OF SULFUR COMPOUNDS FROM A GAS

[75] Inventors: Kenneth J. Frech, Tallmadge; James J. Tazuma, Stow, both of Ohio

[73] Assignee: The Goodyear Tire & Rubber Company, Akron, Ohio

[21] Appl. No.: 130,897

[22] Filed: Mar. 17, 1980

[51] Int. Cl.$^3$ ............................................. B01D 53/34
[52] U.S. Cl. .................................... 423/226; 423/230; 423/243; 423/244
[58] Field of Search ............... 423/226, 228, 229, 230, 423/231, 234, 243, 244 R, 244 A, 242 R, 242 A; 55/73; 260/556 AR

[56] References Cited

U.S. PATENT DOCUMENTS

| | | | |
|---|---|---|---|
| 2,176,196 | 10/1939 | Beamer et al. | 423/234 |
| 2,181,433 | 11/1939 | Jordon | 423/231 |
| 3,756,976 | 9/1973 | Uraneck et al. | 260/29.7 PT |
| 4,035,474 | 7/1977 | Kunkel et al. | 423/574 R |

OTHER PUBLICATIONS

Gilchrist et al., "The Chemistry of Sulfilimines," Chemical Reviews, vol. 77, No. 3, pp. 409–412, 1977.
Tsujihara et al., "Sulfilimine I. Synthesis and Formation Mechanism," Bullet. of the Chemical Society of Japan, vol. 42, pp. 2631–2635, 1969.
Paul et al., "Titrimetric Determination of Mercaptans with Chloramine-T," Talanta, 1975, 22(3), pp. 311–312, (Abstract).
Padma et al., "Chloramine T. I. Oxidation of Some Acyclic Organic Sulfur Compounds," Int. J. Sulfur Chem., Part A, 1971, 1(4), pp. 243–245, (Abstract).

*Primary Examiner*—E. Thomas
*Attorney, Agent, or Firm*—D. O. Nickey

[57] ABSTRACT

This invention relates to a process for the removal of sulfur compounds from a gas stream which consists of contacting said gas stream with alkali metal salts of sulfonamides or resins containing sulfonamide functionalities.

11 Claims, No Drawings

METHOD FOR REMOVAL OF SULFUR COMPOUNDS FROM A GAS

TECHNICAL FIELD

This invention relates to a process for the removal of sulfur compounds from a gas stream. More specifically, this invention describes methods for the sweetening of a sour natural gas stream.

BACKGROUND ART

Removal of sulfur compounds from gas streams has been of considerable importance in the past and is even more so today due to environmental considerations. Gas effluent from the combustion of organic materials, such as coal, almost always contain sulfur compounds and sulfur removal processes have concentrated on removing hydrogen sulfide since it has been considered a significant health hazard and because it is corrosive, particularly when water is present. With increasing emphasis on eliminating or minimizing sulfur discharge to the atmosphere, attention is turning to the removal of other sulfur compounds from gas streams.

The process of the present invention provides a new and effective means for the removal of sulfur compounds from gas streams and is particularly effective in the removal of sulfur compounds from natural gas streams.

Numerous natural gas wells produce what is called in the industry "sour gas." "Sour gas" is natural gas that contains hydrogen sulfide, mercaptans, sulfides and disulfides in concentrations that make its use unacceptable. Considerable effort has been expended to find an effective and cost efficient means to remove these objectionable sulfur compounds from natural gas.

A number of processes are available for removal of $H_2S$ from natural gas streams. Processes presently available can be categorized as those based on physical absorption, solid adsorption, or chemical reaction. Physical absorption processes suffer from the fact that they frequently encounter difficulty in reaching the low concentrations of $H_2S$ required in the sweetened gas stream. Solid bed adsorption processes suffer from the fact that they are generally restricted to low concentrations of $H_2S$ in the entering sour gas stream. Chemically reacting processes in general are able to meet sweet gas $H_2S$ concentrations with little difficulty, however, they suffer from the fact that a material that will react satisfactorily with $H_2S$ will also react with $CO_2$. Above all, the processes presently available do not efficiently provide for removal of mercaptans, sulfides and disulfides.

An example of a chemically reactive process is the ferric oxide fixed bed process, wherein the reactive entity is ferric oxide impregnated on an inert carrier. This process is good for the removal of $H_2S$ but does not appreciably remove mercaptans or other sulfur compounds. The bed can be regenerated, however, the number of regenerations is limited by the build-up of elemental sulfur upon the bed.

A widely used process for removing $H_2S$ from natural gas depends upon the reactivity of $H_2S$ with amino nitrogen, see for example U.S. Pat. No. 1,783,901. In recent years several other patents have been granted covering similar compounds. The amine-like chemical compounds currently being employed for removal of $H_2S$ from gas streams include: monoethanolamine, 2-(2-aminoethoxy)ethanol and diethanolamine. While effective for removal of $H_2S$, these compounds do not effectively remove mercaptans, sulfides or disulfides. Installation costs are high and operating costs are high due to substantial energy requirements.

The Shell Oil Company "Sulfinol" process involves both a physical solvent and a chemically reactive agent in the sweetening solution. The physical solvent involved is tetrahydrothiophene 1,1-dioxide and the amine is normally diisopropylamine. This process suffers from the disadvantage that the physical solvent has a high absorption capacity for the hydrocarbon gas constituents and the cost per unit is excessive.

In general, amine type sweetening processes tend to encounter the same kinds of operating problems, which can be roughly categorized as (a) solution loss, (b) foaming and (c) corrosion. In the presence of water $H_2S$ is corrosive, thus, elimination of corrosion in an amine sweetening unit is all but impossible because most amine type solvents are used in water solution.

Activated carbon and molecular sieves are well-known, however, absorption capacities are limited. Regeneration is possible but this requires sophisticated instrumentation and controls in addition to high energy requirements.

U.S. Pat. No. 4,035,474 discloses a method for removal of sulfur from tail gas by use of a cold bed absorption process. This process utilizes a catalyst, however, catalyst deactivation occurs after 18 hours and a backup unit must be brought on stream while the spent catalyst is regenerated for 12 to 14 hours at 700° F./370° C.

There is an apparent need for an efficient, low-cost gas sweetening process which would remove sulfur compounds from a gas stream effectively and economically. The process of the present invention accomplishes effective and economical removal of sulfur compounds from a gas stream through use of sulfonamide compounds and resins containing pendant sulfonamide functionalities.

The reaction of alkali metal salts of sulfonamides with sulfur compounds is known. For example, a kinetic study of the reaction between sulfides and N-sodium-N-chloro-paratoluene sulfonamide is reported in the *Bull. Chemical Society Japan*, V.42, 2631 (1969), K. Tsujihara, et al. From the mechanistic study of this reaction, a procedure for the synthesis of sulfilimines was devised.

A procedure is disclosed in U.S. Pat. No. 3,756,976 which removes objectionable thiol odor from polymer latex through the use of numerous compounds that convert the odorous sulfur compounds to a nonodorous form. Specifically claimed is the use of the alkali metal salts of N-halogenated arylsulfonamides. U.S. Pat. No. 3,756,976 teaches the use of these compounds to convert the sulfur compounds to a nonodorous form and not the removal thereof. The disclosed process has the converted sulfur compounds within the polymer latex system and does not teach or suggest that sulfur compounds can be removed from a gas stream through use of the alkali metal salts of N-halogenated sulfonamides.

The reaction of sulfides with salts of N-chloroarenesulfonamides was the first method to be discovered for preparing sulfilimines. Gilchrist et al, *Chem. Rev.*, Vol. 77, No. 3, page 409, 1977.

The reaction of Chloramine-T (trade name for N-sodium-N-chloro paratoluene sulfonamide) with thiols, disulfides, sulfides, sulfoxides and sulfones was reported by D. K. Padma et al, in *Int. J. Sulfur Chem.*, Part A 1971, 1(4), 243–50 and titrimetric determination of mercaptans with chloramine-T is reported by R. C. Paul et al. in Talanta, 1975, 22(3), 311-12. All the references cited do not suggest or disclose that salts of sulfonamides such as chloramine-T can be used to remove sulfur compounds from a gas stream.

It is the novel and nonobvious use of alkali metal salts of sulfonamides and resins containing sulfonamide functionalities in a process to remove sulfur compounds from a gas stream that comprises the present invention.

DISCLOSURE OF INVENTION

A process for removing sulfur compounds from a gas stream which comprises contacting said gas stream with a compound of the general structural formula:

wherein Q is selected from the group comprised of alkyl radicals of 1 to 18 carbon atoms, cycloalkyl radicals of 4 to 18 carbon atoms, phenyl radical, mono and dialkyl substituted phenyl radicals wherein the alkyl substituents contain 1 to 6 carbon atoms; and wherein X is selected from the group comprised of chlorine, bromine or iodine radicals and $X_1$ is selected from the group comprised of chlorine, bromine, iodine, hydrogen, sodium, potassium and lithium radicals; or a resin that contains pendant reactive groups of the following structural formula (II):

wherein X is selected from the group comprised of chlorine, bromine or iodine radicals and $X_1$ is selected from the group comprised of chlorine, bromine, iodine, hydrogen, sodium, potassium and lithium radicals.

DETAILED DISCLOSURE OF INVENTION

The means for contacting a gas stream with a compound of general structural formula (I) consists of: spray dispersion of a solution of compound (I), impregnation of a solution of compound (I) on a porous inert carrier, and resins modified to contain functionalities of compound (II).

Spray dispersion of a solution of compound (I) as a means for contacting the gas stream, is accomplished by an aqueous solution of compound (I) when $X_1$ is an alkali metal radical being sprayed under pressure into a treatment vessel through which the sour gas is passing. To one skilled in the art it is obvious that when $X_1$ is a halogen radical or hydrogen, then the solvent would be nonaqueous. The liquid is collected at the bottom of the treatment vessel, rejuvenated and recirculated to the treatment vessel.

A porous carrier such as activated carbon or vermiculite can be used to contact the compounds of formula (I) with the gas stream to be sweetened. The porous carrier is impregnated or loaded by absorption of a solution of compound (I). The process may be repeated after drying the partially loaded carrier so as to obtain the maximum loading.

The impregnated carrier is then placed in the treatment vessel. A solution of compound (I) may be pumped onto the treatment bed during operation to provide continuous bed activity.

Representative of the porous carriers that can be used in the process of this invention are pumice rock, porous clay balls, wood chips, charcoal, vermiculite and carbon granules; vermiculite being the preferred porous carrier.

Resins modified to contain compound (II) functional groups have been prepared which remove sulfur compounds from a gas stream. Polystyrene as an example, was modified by sequential reactions with chlorosulfonic acid, ammonia, and sodium hypochlorite to obtain a resin containing sites which react with and immobilize a variety of sulfur compounds.

The starting resins were commercial polystyrenes, cross-linked by copolymerization with various amounts of divinylbenzene. Representative resins, their properties and suppliers are summarized in Table I.

TABLE I

| Commercial Polystyrene Starting Resins | | |
|---|---|---|
| Resin | Supplier | Structure and Properties |
| Amberlite XAD-2 | Rohm & Haas Co. | Styrene-Divinylbenzene; macroreticular; 90Å avg pore dia; 20-50 mesh; ca 50% $H_2O$. |
| Amberlite XAD-4 | " | Styrene-Divinylbenzene; macroreticular; 50Å avg pore dia; 20-50 mesh; ca 40% $H_2O$. |
| Amberlyst 15 | " | Sulfonated Styrene-Divinylbenzene; ca 4.6 meq $SO_3H$/g; macroreticular; 265Å avg pore dia; 16-50 mesh; <1% $H_2O$. |
| Eastman Cat. No. 11180 | Eastman Kodak Co. | Styrene-Divinylbenzene (2%); gel type; 200-400 mesh; essentially $H_2O$ free. |

All the resins were prepared by variations of the same general technique. The following is illustrative.

Amberlite XAD-4 (See Table I) was washed overnight in flowing water, soaked one hour in reagent grade acetone, washed with diethyl ether, dried briefly at 60° C. and then dried for 3 hours at 105° C. with aspirator vacuum.

32 grams of the purified resin was mixed with 100 ml. of chlorosulfonic acid under a nitrogen blanket. The mixture was heated to 70° C. for one hour and then cooled to 50° C. and then 250 ml. of $CCl_4$ was added and the mixture heated to 70° C. for 1½ hours. The beads were filtered under nitrogen, washed with $CCl_4$ and anhydrous diethyl ether, and then soaked overnight in 250 ml. of anhydrous diethyl ether.

Anhydrous ammonia was slowly bubbled into the resin-ether mixture under nitrogen for 6 hours. After standing overnight, the mixture was stirred 5 hours with 100 ml. of concentrated NH4OH. The beads were filtered, washed with water and heated 2 hours with 600 ml. H2O on a steam bath. During the heating, bromophenol blue indicator was added, followed by periodic additions of concentrated HCl to neutralize any free ammonia. The beads were washed overnight in flowing water, filtered, and dried to constant weight to yield 55.13 grams of intermediate product.

To 25 grams of the product just obtained was added 71 ml. of 2.5 M. NaOCl solution, followed by 5.7 grams NaOH. The temperature of the mixture rose to 53° C. After 1 hour 40 minutes, the liquid was decanted and the resin washed with water, then 71 ml. of NaOCl was added and the mixture was stirred for 2½ hours at 30°-35° C. The resin was filtered and washed for 2½ hours with flowing water and then dried overnight at 40° C., to yield 28.1 grams of product.

The modified resin prepared as above was then placed in the treatment vessel so as to allow for contact between the sour gas stream and the modified resin.

Representative of the alkali metal salts of N-sulfonamides that can be used in the process of this invention are N-sodium-N-chloro-paratoluene sulfonamide, N-sodium-N-chloro-methyl sulfonamide, N, N'dichlorobenzene sulfonamide, N-sodium-N-chlorobenzene sulfonamide, and resins containing these compounds as pendant reactive groups.

More Detailed Disclosure

The process of the present invention can be employed with or without the use of a primary treater. By primary treater is meant a treatment process which eliminates or greatly reduces the amount of H2S in the gas stream prior to treatment by the process of this invention.

As discussed above, numerous processes are presently available that efficiently remove H2S from a gas stream but do not remove other sulfur compounds. Particularly effective for the removal of H2S is the ferric oxide or "iron sponge" process. As a primary treater the ferric oxide process is preferred since the process is effective in the removal of H2S from the gas stream while being economical in operation and set up, however, the ferric oxide primary treatment does lack the ability to remove sulfides, disulfides and mercaptans from a gas stream thus necessitating the use of the process of this invention.

The temperature of the treatment system is maintained at a temperature of at least 0° C. to prevent water vapor from freezing, however, a more preferred temperature range is from 5° to 80° C. with the most preferred range being 5° to 35° C.

The gas flow rate and the volume of the primary treater are such that the retention time in the primary treater is sufficient to remove a major portion of H2S from the gas stream. Those skilled in the art will readily be able to determine the values of the variables in the primary treatment so as to substantially reduce H2S content.

A caustic solution, such as aqueous NaOH, is employed in the primary and secondary treatment vessels for a number of reasons. In the primary treater (if used) relatively high alkalinity is required to maintain optimum performance of the ferric oxide bed in the removal of H2S. In addition, proper alkalinity will allow for removal of some mercaptans by the ferric oxide bed.

Alkalinity of the secondary treater is required so as to facilitate the removal of sulfonamide reaction products from the secondary treatment bed. The presence of aqueous NaOH causes the formation of water soluble sulfonamide salts, which unless removed, would cause the inert carrier to become plugged with reaction product and thus prevent further removal of sulfur compounds from the gas stream. In addition, removal of mercaptans in the secondary treater is more efficient in the presence of aqueous NaOH.

The use of a primary treater in the process of this invention is not essential, however, such use does substantially improve the economics of the secondary treatment in the removal of other sulfur compounds.

The volume and gas flow rate through the secondary treater is such that at from 5° to 35° C. the gas retention time within the secondary treater is at least 30 seconds. To one skilled in the art it is obvious that gas retention times could be increased or decreased depending upon temperature and treatment vessel volumes.

The process of this invention was tested on a high pressure natural gas stream. There would be minor modifications in the process flow for use on low pressure gas, such as coke oven gas or boiler gas, however, the basic principles of operation would remain the same.

The use of compounds of formulae (I) and (II) in the process of this invention provide effective and economical removal of sulfur compounds from a gas stream. As discussed earlier the reaction of sulfonamides with sulfur compounds is well-known, however, all the references and other literature would lead one skilled in the art to believe that use of such compounds in a gas stream would not be possible due to the kinetics of the reaction. The literature discloses liquid phase reactions between sulfonamides and mercaptans with long reaction times and equilibriums far short of complete reaction.

The literature also discloses liquid phase batch reactions between chloramine-T and sulfides in solvents such as alcohols. The reaction times and procedures are such that one skilled in the art would not expect quantitative removal of mercaptans, sulfides and disulfides from gas streams through the use of compounds of formulae (I) and (II) in an aqueous system.

In practice the relatively short contact times in scrubbing gas streams would lead one skilled in the art to believe that quantitative removal of sulfides, mercaptans and disulfides from a gas stream could not be obtained through use of the compounds of formulae (I) and (II). It is the novel use of the compounds of formulae (I) and (II) in the process of removing sulfur compounds from a gas stream that forms the basis of this invention. In addition, the use of the compounds of formulae (I) and (II) in the process of this invention is unique in that the compounds do not lose their effectiveness in the presence of water and are not corrosive to the apparatus when used in conformance with the process of this invention.

BEST MODE FOR CARRYING OUT THE INVENTION

The following examples are intended to illustrate and not to limit the scope of the present invention.

Analysis of the gas stream in the following examples was conducted prior to and subsequent to treatment by the process of this invention. Gas samples were collected in aluminum pressure vessel fitted with quick-connect fittings, valves and gauges. The pressure vessels were then connected to a Barton Recording Sulfur Analyzer Model 286 for measurement of sulfur concentrations.

The Barton 286 Analyzer has a sensitivity of 0.02 ppm of $H_2S$ by volume, 0.02 ppm mercaptans by volume, 0.04 ppm organic sulfides by volume and 0.04 ppm sulfur dioxide with an accuracy of plus or minus 2%. Percent by volume readings were converted to percent by weight and recorded. (ppm=parts/million).

EXAMPLE 1

Ferric Oxide and N-sodium-N-chloro-paratoluene sulfonamide Treatment To Remove Sulfur Compounds From A Natural Gas Stream The primary and secondary treatment vessels used in this experiment are 1.22 meter by 3.05 meter vertical cylindrical vessels with an approximate volume of 3.56 cubic meters for each vessel. The primary treatment vessel was charged with 3.11 cubic meters of redwood chips coated with ferric oxide.

The redwood chips coated with ferric oxide were "IC" Shavings, manufactured and sold by Connelly-GPM, Inc. of Chicago, Illinois, which contain 193.2 kgs of $Fe_2O_3$ per cubic meter. A portion of the ferric oxide chips was added to the vessel, water was added to give a 40% by weight water content and then the chips were compacted by tamping. The process of chip addition, wetting with water and compaction continued until the vessel was filled. The vessel was then closed and made pressure tight. At this point the primary treatment vessel is ready for service.

The secondary treatment vessel was charged with 3.11 cubic meters of expanded vermiculite. The expanded vermiculite was purchased from W. R. Grace, Inc. using the tradename of Zonolite. The secondary vessel was then closed and made pressure tight.

Approximately 190 liters of aqueous 6% chloramine-T (N-sodium-N-chloro paratoluene sulfonamide) solution by weight and 190 liters of aqueous 10% NaOH solution by weight was pumped through spray nozzles onto the vermiculite bed to thoroughly wet the bed. The secondary vessel is now ready for service.

Once the treatment system was pressurized and gas flow began through the vessels, a 6% aqueous solution by weight of chloramine-T was sprayed onto the secondary bed to provide for continuous effective removal of the remaining sulfur compounds from the effluent of the primary treater. To one skilled in this art it is obvious that the amount of aqueous chloramine-T to be sprayed onto the secondary bed will depend upon the gas flow rate, temperature and sulfur content of the gas. Testing the aqueous effluent from the secondary treater with starch iodide paper will indicate when excess chloramine-T solution is being pumped.

To one skilled in the art the amount of caustic solution sprayed onto the secondary bed can easily be determined. Enough caustic solution should be used so as to prevent the formation of insoluble reaction product on the secondary bed. Excess usage of caustic solution can be determined by testing the pH of the effluent from the secondary treater. When the pH exceeds 9.5 more caustic solution is being used than is necessary.

The gas subjected to treatment was taken from a wellhead which produces 84.36 kg/cm² pressure and contains an average of 200 ppm (parts per million) sulfur compounds by weight. A typical wellhead sample, relative to sulfur containing compounds, was found to be:

| S-Compound | ppm by wt. |
|---|---|
| $H_2S$ | 142 |
| $CH_3SH$ | 2 |
| $C_2G_5SH$ | 18 |
| $C_3H_7SH$ | 17 |
| $C_4H_9SH$ | 4–5 |
| Alkyl sulfide | 11–12 |
| $C_5H_{11}SH$ | 4–5 |
| Others | 1–2 |
| Total | 199–203 |

Prior to treatment the gas was separated from any liquid or solid phase material.

The gas pressure at the inlet of the primary treater ranged from 17.0 kg/m² to 17.5 kg/m² and had an average of 200 ppm by weight sulfur compounds.

The gas stream was analyzed after the primary treatment and after the secondary treatment. After a 4 liter per hour pumping rate of 6% aqueous chloramine-T upon the secondary bed was established, pumping of 1 liter per hour 10% NaOH by weight from a separate tank through a nozzle was initiated.

Table I demonstrates that the ferric oxide primary treater can initially reduce the sulfur content of the gas stream from 200 ppm to an average of 40 ppm by weight. Table I also demonstrates that the secondary treater can with addition of the aqueous solution of N-sodium-N-chloro paratoluene sulfonamide and aqueous NaOH continuously remove the remaining sulfur compounds from the gas stream on an industrial scale.

TABLE I

PRIMARY AND SECONDARY TREATMENT

| Day | Flowrate MCF/Day (meters³/day) | Pressure PSIG (Kg/m²) | Fe Sponge Treater Temp: °F./°C. | Chloramine Treater Temp:°F./°C. | Chloramine Input 6% sol. lbs/day(Kg/day) | Sulfur Content Outlet of Prim. Treater ppm by wt.* | Sulfur Content Outlet Second. Treater ppm by wt.** |
|---|---|---|---|---|---|---|---|
| 1 | 350(9905) | 250(17.5) | 58/14.44 | 80/26.67 | 12.5(4.66) | 40 | 18 |
| 2 | 375(10612.5) | 250(17.5) | 62/16.67 | 75/23.89 | 10.7(3.99) | — | 16 |
| 3 | 400(11320) | 245(17.15) | 63/17.22 | 78/25.56 | 10.2(3.81) | 41 | 15 |
| 4 | 400(11320) | 245(17.15) | 65/18.33 | 79/26.11 | 10.5(3.92) | — | 16 |
| 6 | 525(14857.5) | 250(17.5) | 65/18.33 | 79/26.11 | 12.0(4.48) | — | 17 |
| 7 | 550(15565) | 250(17.5) | 67/19.44 | 80/26.67 | 12.9(4.81) | 40 | 18 |
| 9 | 625(17687.5) | 250(17.5) | 64/17.78 | 78/25.56 | 14.0(5.22) | — | 19 |
| 10 | 650(18395) | 245(17.15) | 66/18.89 | 76/24.44 | 13.8(5.15) | 41 | 18 |
| 12 | 675(19102.5) | 250(17.5) | 66/18.89 | 77/25.00 | 14.1(5.26) | — | 20 |

*Data for sulfur content out of primary treater was obtained by taking batch samples and analyzing on the Barton Titrimeter.
**Data for sulfur content at the outlet of the secondary treater was obtained via continuous sample flow to the Barton Titrimeter.

EXAMPLE 2

Example 2 is an illustration of the use of compounds of Formula (I) to remove sulfur compounds from a gas stream without primary treatment. The primary treatment vessel was by-passed and the untreated gas stream containing an average of 200 ppm sulfur by weight was fed directly into the secondary treater as in Example 1. Table II contains the data collected on this two day test run.

TABLE II

| Secondary Treatment Alone | | |
|---|---|---|
| | Day (1) | Day (2) |
| Flow Rate cu. meter/day | 15,565 | 16,980 |
| Pressure Kg/sq. cm. | 17.5 | 17.5 |
| Treater Temp. °C. | 29.4 | 30.6 |
| Chloramine-T Input Kg/day | 7.5 | 6.7 |
| S Content to Treater ppm by wt. | 200 | 200 |
| S Content from Treater ppm by wt. | 30 | 29 |

From Table II it is evident that compounds of Formula (I) may be used to remove sulfur compounds from a gas stream without the use of a primary treater.

EXAMPLE 3

The primary and secondary treatment vessels were prepared as in Example 1. The data collected is shown on Table III. Pumping of a 10% aqueous solution, chloramine-T, by weight was not begun until the effluent from the secondary treater contained 45 ppm sulfur compounds by weight. For eleven days after the addition of the chloramine-T solution began the average sulfur content of the effluent from the secondary treater was 2 ppm by weight.

Table III demonstrates that the process of this invention can substantially reduce the sulfur content of a natural gas stream on an industrial scale.

TABLE III

| | | | Example 3 | |
|---|---|---|---|---|
| | | | Secondary Treater | |
| Day | Gas Throughput: (meters$^3$) | Pressure: Psig | Gas Feed to Test Treater Sulfur Content: ppm by wt | Effluent from Test Treater Sulfur Content: ppm by wt. |
| 1 | 1,900 (53.80) | 156 | 73 | <5 |
| 2 | 3,700 (104.71) | 160 | — | <5 |
| 3 | 5,500 (155.65) | 155 | — | 21 |
| 4 | 7,100 (200.93) | 154 | 72 | 45 |
| Began pumping 0.5 cc/min of 10% Chloramine-T Solution | | | | |
| 5 | 9,200 (260.36) | 170 | — | 2 |
| 6 | 10,500 (297.15) | 178 | — | 2 |
| 8 | 13,300 (376.39) | 158 | 74 | 1 |
| 10 | 16,100 (455.63) | 182 | — | 3 |
| 12 | 20,100 (568.83) | 192 | — | 2 |
| 14 | 24,000 (679.20) | 180 | — | 2 |
| 16 | 28,200 (798.06) | 175 | — | 1 |
| | | AVERAGE | 73 (During Pumping) | 2 |

Industrial Applicability

The process of this invention which employs the use of compounds of Formulae (I) and (II) has numerous industrial applications. The need for an effective and economical means for removing H₂S, sulfides, disulfides and mercaptans from a gas stream has been long felt. Through the use of this invention sulfur compounds can be removed from a gas stream, for example, effluent from coke ovens, sewage plants, paper mills and in particular sour natural gas streams. Conversely, this invention can be used to remove sulfur compounds from gas streams entering vessels, hospitals, buildings and etc.

While certain representative embodiments and details have been shown for the purpose of illustrating the invention, it will be apparent to those skilled in this art that various changes and modifications may be made therein without departing from the spirit or scope of the invention.

We claim:

1. A process for removing hydrogen sulfide, mercaptans, sulfides and disulfides from a gas stream which comprises contacting said gas stream with a compound of the structural formula (I):

wherein Q is selected from the group comprised of alkyl radicals of 1 to 18 carbon atoms, cycloalkyl radicals of 4 to 18 carbon atoms, phenyl radical, mono and dialkyl substituted phenyl radicals wherein the alkyl substituents contain 1 to 6 carbon atoms; and wherein X is selected from the group comprised of chlorine, bromine or iodine radicals and $X_1$ is selected from the group comprised of chlorine, bromine, iodine, hydrogen, sodium, potassium and lithium radicals.

2. A process according to claim 1 wherein Q of formula (I) is the radical

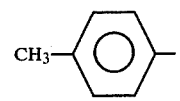

and X is a chlorine radical and $X_1$ is a sodium radical.

3. A process according to claim 1 wherein the gas stream is contacted with a compound of formula (I) by:
   a. spraying a solution of compound (I) into the gas stream to form a dispersion thereof, or
   b. impregnation of a solution of compound (I) on porous inert carrier wherein the porous inert carrier is selected from the group comprised of pumice rock, porous clay balls, wood chips, charcoal, vermiculite and carbon granules.

4. A process according to claim 1 wherein the gas stream being contacted with a compound of formula (I)

is pretreated so as to substantially remove the H₂S content of the gas stream.

5. A process according to claim 1 wherein a solution of NaOH or KOH is added before and/or during contacting said gas stream with a compound of structural formula (I), in an amount and rate sufficient to prevent the formation of insoluble reaction products.

6. A process for removing hydrogen sulfide, mercaptans, sulfides and disulfides from a gas stream which comprises contacting said gas stream with a resin that contains pendant reactive groups of the structural formula:

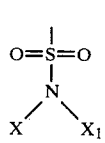 (II)

wherein X is selected from the group comprised of chlorine, bromine or iodine radicals and $X_1$ is selected from the group comprised of chlorine, bromine, iodine, hydrogen, sodium, lithium and potassium radicals.

7. A process according to claim 6 wherein a solution of NaOH or KOH is added before and/or during contacting said gas stream with a compound of structural formula (II), in an amount and rate sufficient to prevent the formation of insoluble reaction products.

8. A process according to claim 6 wherein the gas stream being contacted with a compound of formula (II) is pretreated so as to substantially remove the H₂S content of the gas stream.

9. A process according to claim 6 wherein X of formula (II) is a chlorine radical and $X_1$ is a sodium radical.

10. A process for removing hydrogen sulfides, mercaptans, sulfides and disulfides from a gas stream which comprises:
(a) contacting said gas stream with ferric oxide impregnated on an inert carrier in the presence of a caustic solution, so as to substantially reduce the H₂S content of said gas stream, then subsequently
(b) contacting said gas stream with a compound of the structural formula

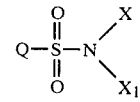 (I)

wherein Q is selected from the group comprised of alkyl radicals of 1 to 18 carbon atoms, cycloalkyl radicals of 4 to 18 carbon atoms, phenyl radical, mono and dialkyl substituted phenyl radicals wherein the alkyl substituents contain 1 to 6 carbon atoms; and wherein X is selected from the group comprised of chlorine, bromine or iodine radicals and $X_1$ is selected from the group comprised of chlorine, bromine, iodine, hydrogen, sodium, potassium and lithium radicals; impregnated on an inert carrier in the presence of a caustic solution.

11. A process according to claim 10 wherein the compound of formul (I) is N-sodium-N-chloro-paratoluene sulfonamide.

* * * * *